United States Patent
Agarwal et al.

(10) Patent No.: US 11,517,740 B2
(45) Date of Patent: Dec. 6, 2022

(54) METHODS FOR CONTROLLING A LEFT VENTRICULAR ASSIST DEVICE

(71) Applicant: TC1 LLC, St. Paul, MN (US)

(72) Inventors: Rahul Agarwal, Los Angeles, CA (US); Allison Connolly, Fremont, CA (US); Yelena Nabutovsky, Mountain View, CA (US); Julie Prillinger, Redwood City, CA (US)

(73) Assignee: TC1 LLC, St. Paul, MN (US)

( * ) Notice: Subject to any disclaimer, the term of this patent is extended or adjusted under 35 U.S.C. 154(b) by 431 days.

(21) Appl. No.: 16/354,922

(22) Filed: Mar. 15, 2019

(65) Prior Publication Data
US 2019/0282743 A1 Sep. 19, 2019

Related U.S. Application Data

(60) Provisional application No. 62/643,545, filed on Mar. 15, 2018.

(51) Int. Cl.
*A61M 60/50* (2021.01)
*A61B 5/0215* (2006.01)
(Continued)

(52) U.S. Cl.
CPC ........... *A61M 60/50* (2021.01); *A61B 5/0215* (2013.01); *A61B 5/742* (2013.01); *A61B 5/7405* (2013.01);
(Continued)

(58) Field of Classification Search
CPC .......................... A61M 1/1086; A61B 5/0215
See application file for complete search history.

(56) References Cited

U.S. PATENT DOCUMENTS 3,911,897 A 10/1975 Leachman
5,139,517 A 8/1992 Corral
(Continued)

FOREIGN PATENT DOCUMENTS

EP 2 570 143 A1 3/2013
EP 3 213 781 A1 9/2017
(Continued)

OTHER PUBLICATIONS

Zavarella, How to Better Evaluate the Goodness-of-Fit of Regressions, Online <https://medium.com/microsoftazure/how-to-better-evaluate-the-goodness-of-fit-of-regressions-990dbf1c0091> (Year: 2017).*

(Continued)

*Primary Examiner* — Rex R Holmes
*Assistant Examiner* — Sana Sahand
(74) *Attorney, Agent, or Firm* — Kilpatrick Townsend & Stockton LLP

(57) ABSTRACT

The present invention is generally related to methods and systems for preventing onset or worsening of RHF in patients with implanted ventricular assist devices. More particularly, the present invention relates to identifying patients at risk for RHF following implantation of a ventricular assist device based on pulmonary artery pressure measurement and/or trends and adjusting a pump operating parameter to prevent or reduce the onset or worsening of RHF in such patients, improve patient outcomes, or reduce mortality risks associated with VAD implantation. In particular, a pump operating parameter may be adjusted to reduce or minimize particularly high pressure loads on a patient's heart or amount of time the patient is exposed to such high pressure loads following implantation.

18 Claims, 10 Drawing Sheets

(51) Int. Cl.
*A61B 5/00* (2006.01)
*A61M 60/148* (2021.01)

(52) U.S. Cl.
CPC ......... *A61B 5/7455* (2013.01); *A61M 60/148* (2021.01); *A61M 2205/0244* (2013.01); *A61M 2205/18* (2013.01); *A61M 2205/3331* (2013.01); *A61M 2205/3334* (2013.01); *A61M 2205/50* (2013.01); *A61M 2205/581* (2013.01); *A61M 2205/582* (2013.01); *A61M 2205/583* (2013.01); *A61M 2230/30* (2013.01)

(56) References Cited

U.S. PATENT DOCUMENTS

| | | |
|---|---|---|
| 5,318,592 A | 6/1994 | Schaldach |
| 5,503,615 A | 4/1996 | Goldstein |
| 6,066,086 A | 5/2000 | Antaki et al. |
| 6,111,520 A | 8/2000 | Allen et al. |
| 6,278,379 B1 | 8/2001 | Allen et al. |
| 6,585,635 B1 | 7/2003 | Aldrich |
| 6,634,224 B1 | 10/2003 | Schoeb et al. |
| 6,643,420 B2 | 11/2003 | Han et al. |
| 6,772,011 B2 | 8/2004 | Dolgin et al. |
| 6,855,115 B2 | 2/2005 | Fonseca et al. |
| 6,984,201 B2 | 1/2006 | Khaghani et al. |
| 7,029,433 B2 | 4/2006 | Chang |
| 7,245,117 B1 | 7/2007 | Joy et al. |
| 7,320,706 B2 | 1/2008 | Ai-Najjar |
| 7,439,723 B2 | 10/2008 | Allen et al. |
| 7,498,799 B2 | 3/2009 | Allen et al. |
| 7,520,850 B2 | 4/2009 | Brockway |
| 7,550,978 B2 | 6/2009 | Joy et al. |
| 7,679,355 B2 | 3/2010 | Allen et al. |
| 7,839,153 B2 | 11/2010 | Joy et al. |
| 7,853,325 B2 | 12/2010 | Dabney et al. |
| 7,862,501 B2 | 1/2011 | Woodard |
| 7,945,333 B2 | 5/2011 | Jacobson |
| 7,963,905 B2 | 6/2011 | Salmonsen et al. |
| 7,988,728 B2 | 8/2011 | Ayre |
| 7,998,054 B2 | 8/2011 | Bolling |
| 8,145,324 B1 | 3/2012 | Stevenson et al. |
| 8,177,838 B2 | 5/2012 | Vodermayer et al. |
| 8,180,448 B2 | 5/2012 | Stevenson et al. |
| 8,224,462 B2 | 7/2012 | Westlund et al. |
| 8,246,530 B2 | 8/2012 | Sullivan |
| 8,295,939 B2 | 10/2012 | Jacobson |
| 8,364,283 B2 | 1/2013 | Halperin et al. |
| 8,506,471 B2 | 8/2013 | Bourque |
| 8,543,205 B2 | 9/2013 | Ostroff |
| 8,608,636 B2 | 12/2013 | Choi et al. |
| 8,657,733 B2 | 2/2014 | Ayre et al. |
| 8,682,431 B2 | 3/2014 | Callaway et al. |
| 8,712,544 B2 | 4/2014 | Dabney et al. |
| 8,771,165 B2 | 7/2014 | Choi et al. |
| 8,794,989 B2 | 8/2014 | Kearsley et al. |
| 8,852,099 B2 | 10/2014 | Von Arx et al. |
| 8,864,644 B2 | 10/2014 | Yomtov |
| 8,894,561 B2 | 11/2014 | Callaway et al. |
| 8,897,887 B2 | 11/2014 | Halperin et al. |
| 9,039,595 B2 | 5/2015 | Ayre et al. |
| 9,090,271 B2 | 7/2015 | Bartonek |
| 9,387,284 B2 | 7/2016 | Heilman et al. |
| 9,433,714 B2 | 9/2016 | Voskoboynikov et al. |
| 9,579,432 B2 | 2/2017 | Tamez et al. |
| 9,579,435 B2 | 2/2017 | Yomtov |
| 9,592,327 B2 | 3/2017 | Wariar et al. |
| 9,833,552 B2 | 12/2017 | Yomtov |
| 2005/0071001 A1 | 3/2005 | Jarvik |
| 2007/0088397 A1 | 4/2007 | Jacobson |
| 2008/0097226 A1* | 4/2008 | McConnell .......... A61B 5/0031 600/485 |
| 2008/0281146 A1 | 11/2008 | Morello |
| 2009/0118783 A1* | 5/2009 | Patangay ........... A61N 1/36564 607/18 |
| 2010/0222632 A1* | 9/2010 | Poirier ............... A61M 1/1086 600/16 |
| 2010/0222833 A1* | 9/2010 | Salo ................... A61N 1/36564 607/6 |
| 2010/0241223 A1 | 9/2010 | Lee et al. |
| 2011/0077574 A1* | 3/2011 | Sigg ................... A61M 1/3403 604/6.01 |
| 2011/0178361 A1 | 7/2011 | Yomtov |
| 2011/0270331 A1 | 11/2011 | Peters et al. |
| 2013/0072846 A1 | 3/2013 | Heide et al. |
| 2014/0012067 A1 | 1/2014 | Poirier |
| 2014/0046120 A1 | 2/2014 | Choi et al. |
| 2014/0058190 A1 | 2/2014 | Gohean et al. |
| 2014/0188148 A1 | 7/2014 | Le Blanc et al. |
| 2015/0057488 A1 | 2/2015 | Yomtov |
| 2015/0073203 A1 | 3/2015 | Wariar et al. |
| 2015/0148587 A1 | 5/2015 | Bourque |
| 2015/0151032 A1 | 6/2015 | Voskoboynikov et al. |
| 2015/0174307 A1 | 6/2015 | Eckman et al. |
| 2015/0290374 A1 | 10/2015 | Bourque et al. |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0228628 A1 | 8/2016 | Medvedev et al. |
| 2016/0263299 A1 | 9/2016 | Xu et al. |
| 2017/0021070 A1 | 1/2017 | Petersen |
| 2017/0080138 A1 | 3/2017 | Yomtov |
| 2018/0050348 A1 | 2/2018 | Whitney |
| 2018/0078689 A1 | 3/2018 | Yomtov |
| 2018/0140760 A1 | 5/2018 | Cotter |
| 2018/0280599 A1 | 10/2018 | Harjes et al. |
| 2018/0280600 A1 | 10/2018 | Harjes et al. |
| 2018/0280601 A1 | 10/2018 | Harjes et al. |
| 2018/0353667 A1* | 12/2018 | Moyer ................. A61M 60/50 |

FOREIGN PATENT DOCUMENTS

| | | | |
|---|---|---|---|
| EP | 3213781 A1 * | 9/2017 | .......... A61M 60/148 |
| WO | 2007089500 A2 | 8/2007 | |
| WO | 2011123789 A1 | 10/2011 | |
| WO | 2016001284 A2 | 1/2016 | |
| WO | 2016137743 A1 | 9/2016 | |
| WO | 2017117185 A1 | 7/2017 | |
| WO | 2017117215 A1 | 7/2017 | |
| WO | 2017139113 A1 | 8/2017 | |

OTHER PUBLICATIONS

Bedi et al., "Ventricular Arrhythmias During Left Ventricular Assist Device Support", Am J Cardiol., vol. 99, Issue 8, 2007, pp. 1151-1153.

Brisco et al., "The Incidence, Risk, and Consequences of Atrial Arrhythmias In Patients With Continuous-flow Left Ventricular Assist Devices", J Card Surg, vol. 29, Issue 4, 2014, pp. 572-580.

Clark et al., "Hemodynamic Effects of An Irregular Sequence of Ventricular Cycle Lengths During Atrial Fibrillation", Journal of the American College of Cardiology, vol. 30, Issue 4, 2007, pp. 1039-1045.

Enriquez et al., "Clinical Impact of Atrial Fibrillation In Patients With The Heartmate li Left Ventricular Assist Device", Journal of the American College of Cardiology, vol. 64, Issue 18, 2014, pp. 1883-1890.

Hayward et al., "Effect of Alteration In Pump Speed on Pump Output and Left Ventricular Filling With Continuous-flow Left Ventricular Assist Device", ASAIO Journal. vol. 57, issue 6, 2011, pp. 495-500.

Maeda et al., "Predictive Control by Physical Activity Rate of a Total Artificial Heart During Exercise", Transactions of the American Society of Artificial Internal Organs, vol. 34, 1988, pp. 480-484.

Maury et al., "First Experience of Percutaneous Radio-frequency Ablation for Atrial Flutter and Atrial Fibrillation In A Patient With Heartmate li Left Ventricular Assist Device", Journal of Interventional Cardiac Electrophysiology, vol. 29, Issue 1, 2010, pp. 63-67.

(56) References Cited

OTHER PUBLICATIONS

Oswald et al., "Implantable Defibrillator Therapy for Ventricular Tachyarrhythmia In Left Ventricular Assist Device Patients", Eur J Heart Fail., vol. 12, Issue 6, 2010, pp. 593-599.
Oz et al., "Malignant Ventricular Arrhythmias Are Well Tolerated In Patients Receiving Long-term Left Ventricular Assist Devices", Journal of the American College of Cardiology, vol. 24, Issue 7, 1994, pp. 1688-1691.
Raasch et al., "Epidemiology, Management, and Outcomes of Sustained Ventricular Arrhythmias After Continuous-flow Left Ventricular Assist Device Implantation", Am Heart J., vol. 164, Issue 3, 2012, pp. 373-378.
Ziv et al., "Effects of Left Ventricular Assist Device Therapy on Ventricular Arrhythmias", Journal of the American College of Cardiology, vol. 45, Issue 9, 2005, pp. 1428-1434.

\* cited by examiner

| $\Delta\alpha \backslash \Delta p$ | $-th_{p2} \leq \Delta p \leq -th_{p1}$ | $-th_{p1} < \Delta p \leq -th_{p0}$ | $-th_{p0} < \Delta p < +th_{p0}$ | $+th_{p0} \leq \Delta p < +th_{p1}$ | $+th_{p1} \leq \Delta p \leq +th_{p2}$ |
|---|---|---|---|---|---|
| $-th_{\alpha2} \leq \Delta\alpha \leq -th_{\alpha1}$ | Decrease 6 | Decrease 1 | No change | Increase 5 | Increase 10 |
| $-th_{\alpha1} < \Delta\alpha \leq -th_{\alpha0}$ | Decrease 7 | Decrease 2 | No change | Increase 4 | Increase 9 |
| $-th_{\alpha0} < \Delta\alpha < +th_{\alpha0}$ | Decrease 8 | Decrease 3 | No change | Increase 3 | Increase 8 |
| $+th_{\alpha0} \leq \Delta\alpha < +th_{\alpha1}$ | Decrease 9 | Decrease 4 | No change | Increase 2 | Increase 7 |
| $+th_{\alpha1} \leq \Delta\alpha \leq +th_{\alpha2}$ | Decrease 10 | Decrease 5 | No change | Increase 1 | Increase 6 |

FIG. 4

METHODS FOR CONTROLLING A LEFT VENTRICULAR ASSIST DEVICE

CROSS REFERENCE TO RELATED APPLICATIONS

The present application claims the benefit under 35 USC § 119(e) of U.S. Provisional Appln. No. 62/643,545 filed Mar. 15, 2018, the full disclosure of which is incorporated herein by reference in its entirety for all purposes.

BACKGROUND

This application relates generally to methods and systems for preventing the onset or worsening of right heart failure in patients with implanted ventricular assist devices, and more particularly to identifying patients at risk for right heart failure following implantation of a ventricular assist device based on pulmonary artery pressure measurement and/or trends and adjusting therapy to prevent or reduce the onset or worsening of right heart failure in such patients.

Ventricular assist devices, known generally as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

However, some studies show that left ventricular assist device (LVAD) patients may have high mortality rates in the first year of the LVAD implantation. One of the main contributors to these mortality risks is right heart failure (RHF), which potentially accounts for 20-50% of LVAD-related deaths. Currently, strategies used to address RHF, when it occurs, include managing the preload and afterload of the right ventricle of a patient with inotropic support. However, increased use of inotropes may also be associated with an increased risk of mortality.

Therefore, there is a continuing need for improved methods and systems to reduce mortality risks related to poor management of RHF in LVAD patients, particularly during the first year of implantation. The present invention provides improved methods and systems for identifying patients at risk for new or worsening RHF following LVAD implantation and adjusting therapy to prevent such onset or worsening of RHF and to reduce mortality risks.

BRIEF SUMMARY

The present invention is generally related to methods and systems for preventing onset or worsening of RHF in patients with implanted ventricular assist devices. More particularly, the present invention relates to identifying patients at risk for RHF following implantation of a ventricular assist device based on pulmonary artery (PA) pressure measurement and/or trends (e.g. a PA pressure profile or curve) and adjusting therapy (e.g., blood pump operating parameter) to prevent or reduce the onset or worsening of RHF in such patients, improve patient outcomes, and reduce mortality risks associated with VAD implantation.

In some embodiments, a method of identifying a patient at risk for RHF following implant of a blood pump is provided based on PA pressure trends. In further embodiments, a method of preventing onset and/or worsening of RHF based on PA pressure trends is provided for patients with implanted blood pumps. In yet further embodiments, a blood pump system is provided that may monitor physiological parameters (e.g., PA pressure trends) of the patient and may adjust a pumping operation (e.g., speed, mode, flow rate, or the like) in response to the monitored parameters and/or may report the monitored parameters to a physician or clinician to adjust the pumping.

Pulmonary artery pressure measurements can provide a host of valuable data that may be directly applicable for determining a patient's hemodynamic state, identifying patients at risk for RHF, and optimizing blood pump settings or parameters to prevent onset or worsening of RHF. For example, based on historical data collected from patients that responded well to LVAD therapy, a transient period was observed in the first couple weeks post-LVAD implant during which PA pressures were significantly reduced compared to pre-LVAD implant levels. This transient period was followed by a plateau of PA pressures (e.g., stabilization onto lower pressures compared to pre-LVAD implant levels), called a stable period. An ideal PA pressure curve or profile may be derived from this historical pressure data of patients that responded well to LVAD therapy. A pressure curve or profile derived from PA pressure measurements of a current patient following LVAD implant may then be compared to the ideal PA pressure curve. Clinicians may then use this data, depending on differences between the curves (e.g., the stabilization of PA pressures outside a pre-determined target zone or designated time period), to identify a patient at risk for new or worsening RHF and adjust LVAD therapy accordingly (e.g., increase or decrease LVAD flow rate or change heart failure medications) to optimize treatment to prevent such onset or worsening of RHF in the patient.

In some embodiments of the present invention, a method for reducing risk of right heart failure (RHF) in a patient following implantation of a blood pump system is provided that includes receiving a plurality of pulmonary artery (PA) pressure measurements or PA trending data, fitting a regression model to the plurality of PA pressure measurements or PA trending data, and determining a deviation between at least one estimated parameter and at least one ideal parameter. The at least one estimated parameter is computed from the regression model. The method further includes adjusting at least one operating parameter of a blood pump based on the determined deviation.

The method may include identifying if a patient is at risk for RHF based on the received plurality of PA pressure measurements or PA trending data. In some embodiments, the at least one operating parameter is adjusted only if the patient is identified at risk for RHF.

The method may further include determining a goodness of fit of the regression model and comparing the goodness of fit of the regression model to a threshold value prior to determining the deviation between the at least one estimated and ideal parameters. The method may also include collecting additional PA pressure measurements or PA trending data when the goodness of fit exceeds the threshold value. In some embodiments, the method only includes determining the deviation between the at least one estimated and ideal parameters when the goodness of fit is less than the threshold value.

In certain embodiments, the at least one ideal parameter is computed by fitting the regression model to historical PA pressure measurements or PA trending data of a patient population. In certain aspects of the invention, the plurality of PA pressure measurements or PA trending data are received only during a transient period of time following implantation of the blood pump. The transient period of time may last for less than about 20 days following implantation of the blood pump prior to transitioning to a stable or steady state period.

In some embodiments, determining the deviation between the at least one estimated and ideal parameters includes computing a deviation between an estimated steady state pressure and an ideal steady state pressure.

In some embodiments, adjusting the at least one operating parameter of the blood pump includes increasing a flow rate when the determined deviation between the at least one estimated steady state pressure and the at least one ideal steady state pressure exceeds a threshold value. In other embodiments, adjusting the at least one operating parameter of the blood pump includes decreasing a flow rate when the computed deviation between the estimated steady state pressure and the ideal steady state pressure is less than a threshold value.

Adjusting the at least one operating parameter of the blood pump may include adjusting at least one of a flow rate, pump speed, or a pumping operation mode. Further, adjusting the pumping operation mode may include adjusting at least one of continuous pumping or pulsatile pumping.

In certain embodiments, the regression model is defined by: $p(t)=p_\infty+e^{-\alpha t}(p_0-p_\infty)$, wherein: $p(t)$ are the received PA pressure measurements or PA trending data after implantation of the blood pump; $p_0$ is estimated baseline PA pressure prior to implantation of the blood pump; $p_\infty$ is estimated steady state pressure; and $\alpha$ is an estimated time constant.

In some embodiments, the plurality of PA pressure measurements or PA trending data is wirelessly transmitted by a MEMS based pressure sensor implanted within the pulmonary artery or an interrogation unit associated therewith.

In some embodiments, the method includes determining a responsiveness of the patient to the blood pump system based on the determined deviation prior to adjusting the at least one operating parameter of the blood pump. In some embodiments, the PA trending data includes a PA pressure profile or curve.

In certain embodiments, the at least one estimated and ideal parameters include at least one of a pressure or time parameter. The pressure parameter may be a steady state or stabilization period pressure and the time parameter may be a transient duration period.

In some embodiments, at least one of an external heart blood pump controller, an implantable heart blood pump controller, or an external computing device are provided and configured to carry out steps of the method. In some embodiments, at least one of an external heart blood pump controller, an implantable heart blood pump controller, or an external computing device are separate devices from the blood pump or pressure sensor.

In some embodiments, adjustment of the at least one operating parameter of the blood pump stabilizes PA pressure during a transient period of time. In further embodiments, the method includes outputting at least one of a visual, audio, or haptic alert prior to adjustment of the at least one operating parameter of the blood pump.

In other aspects of the invention, a method for reducing risk of right heart failure (RHF) in a patient following implantation of a blood pump system is provided that includes: receiving a plurality of pulmonary artery (PA) pressure measurements or PA trending data; fitting a regression model to the plurality of PA pressure measurements or PA trending data; determining a deviation between at least one estimated parameter and at least one ideal parameter, wherein the at least one estimated parameter is computed from the regression model; and outputting an alert to adjust at least one operating parameter of a blood pump based on the determined deviation. In some embodiments, the method includes outputting at least one of the plurality of PA pressure measurements, PA trending data, or determined deviation onto a display.

In other aspects of the invention, a method for reducing risk of right heart failure (RHF) in a patient following implantation of a blood pump system includes: receiving a plurality of pulmonary artery (PA) pressure measurements from a pressure sensor positioned in the PA of a patient; estimating a steady state pressure of the patient from the plurality of PA pressure measurements; determining a deviation between the estimated steady state pressure and an ideal steady state pressure; and adjusting at least one operating parameter of a blood pump based on the determined deviation.

In further embodiments, a blood pump system is provided that is configured to reduce a risk of right heart failure (RHF) in a patient following implantation of a blood pump in the patient and includes: a controller operably coupled with the blood pump and configured to receive a plurality of pulmonary artery (PA) pressure measurements or PA trending data from an implantable cardiac electronic device; fit a regression model to the plurality of PA pressure measurements or PA trending data; determine a deviation between at least one estimated parameter and at least one ideal parameter, wherein the at least one estimated parameter is computed from the regression model; and adjust at least one operating parameter of the blood pump based on the determined deviation.

In some embodiments, the controller includes at least one of an external heart blood pump controller, an implantable heart blood pump controller, or external computing device. The system may further include the implantable cardiac electronic device. The implantable cardiac electronic device may include a pressure sensor. In some embodiments, the system includes an interrogation unit configured to interrogate the implantable cardiac electronic device. The interrogation unit may be operably coupled to the controller.

In some embodiments, at least one of the controller, implantable cardiac electronic device, or interrogation unit are in electrical communication with a power source. Two or more of the controller, implantable cardiac electronic device, or interrogation unit share a power source. In certain embodiments, the controller and implantable cardiac electronic device are configured to communicate wirelessly.

In some embodiments, the controller is configured to determine a goodness of fit of the regression model and compare the goodness of fit of the regression model to a threshold value prior to determining the deviation between the at least one estimated and ideal parameters. The controller may be configured to collect additional PA pressure measurements or PA trending data when the goodness of fit exceeds the threshold value. In some embodiments, the controller is configured to only determine the deviation between the at least one estimated and ideal parameters when the goodness of fit is less than the threshold value.

In some embodiments, the plurality of PA pressure measurements or PA trending data are configured to be received by the controller only during a transient period of time following implantation of the blood pump. In further embodiments, the controller is configured to determine the deviation between the at least one estimated and ideal parameters by computing a deviation between an estimated steady state pressure and an ideal steady state pressure. In some embodiments, the controller is configured to increase a flow rate when the determined deviation between the at least one estimated steady state pressure and the at least one ideal steady state pressure exceeds a threshold value. In other embodiments, the controller is configured to decrease a flow rate when the computed deviation between the estimated steady state pressure and the ideal steady state pressure is less than a threshold value. In yet further embodiments, the controller is configured to adjust the at least one operating parameter of the blood pump by adjusting at least one of a flow rate, pump speed, or a pumping operation mode.

In certain embodiments, the regression model is defined by: $p(t)=p_\infty+e^{-\alpha t}(p_0-p_\infty)$, wherein: p(t) are the received PA pressure measurements or PA trending data after implantation of the blood pump; $p_0$ is estimated baseline PA pressure prior to implantation of the blood pump; $p_\infty$ is estimated steady state pressure; and $\propto$ is an estimated time constant.

In certain embodiments, the controller includes a display and is configured to output at least one of a visual, audio, or haptic alert prior to adjustment of the at least one operating parameter of the blood pump. The controller may include an interrogation unit configured to interrogate the implantable cardiac electronic device. The controller may include a processor, memory, antenna, or transceiver. In some embodiments, the memory is configured to store at least one of the PA pressure measurements, PA trend data, ideal parameter, or threshold values. In some embodiments, the controller is configured as a first controller operably coupled to a second controller, wherein the first controller is configured to receive the PA pressure measurements or PA trend data and the second controller is configured to adjust the at least one operating parameter of the blood pump.

BRIEF DESCRIPTION OF THE DRAWINGS

FIG. 4 illustrates an exemplary table corresponding to FIG. 3 of change in relative LVAD flow rates based on calculated deviations and thresholds.

DETAILED DESCRIPTION

Figure 1A:
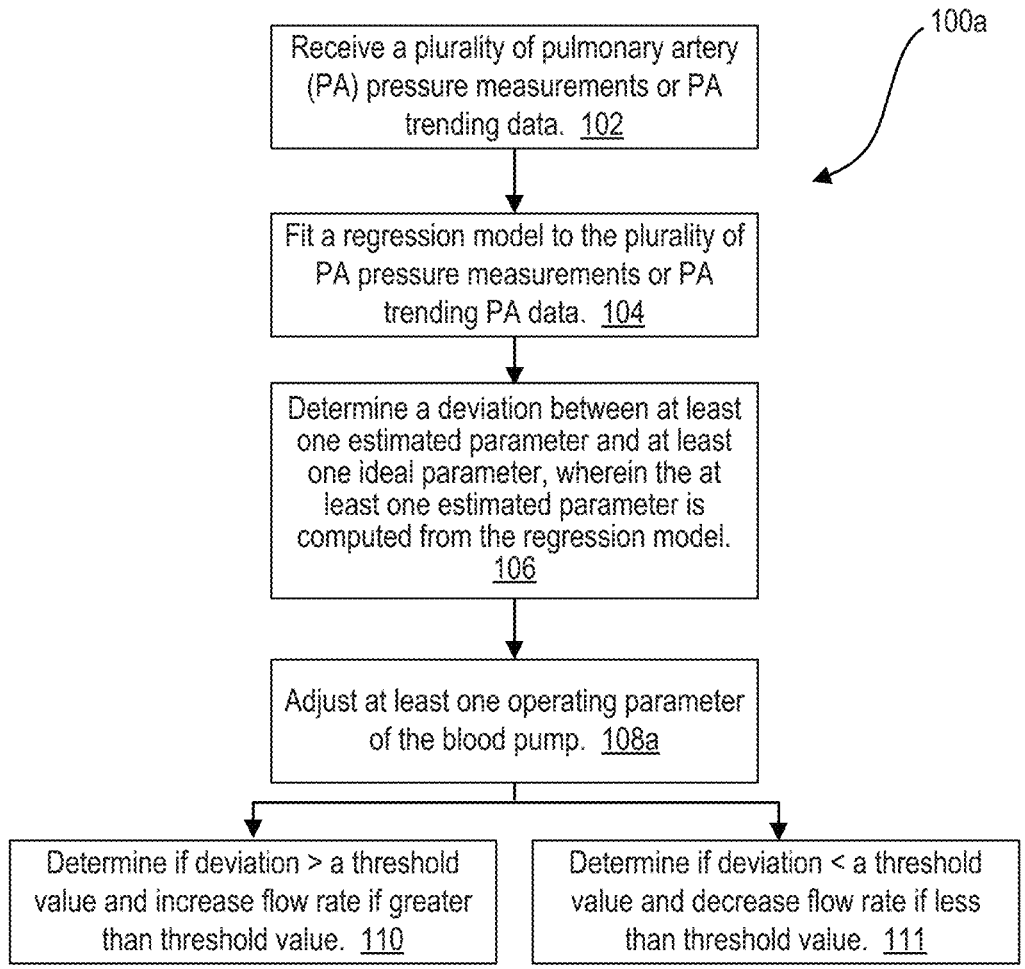
FIGS. 1A-1F illustrate exemplary methods according to some embodiments as described herein.

FIGS. 1A-1F illustrate exemplary methods 100a-100f for preventing onset or worsening RHF following implant of a LVAD according to some embodiments. One or more of any steps of methods 100a-100f as described herein may be included, combined, or substituted within any of the other methods. With reference to FIG. 1A, exemplary method 100a may include receiving a plurality of PA pressure measurements or PA pressure trending data 102, 102f of a patient with an implanted LVAD. These measurements or data may be received from or collected by an implantable cardiac medical device (e.g., a pressure sensor) implanted within the pulmonary artery of the patient as described in more detail below. The method 100a further includes fitting a regression model (e.g., $p(t)=p_\infty+e^{-\alpha t}(p_0-p_\infty)$) to the pressure measurements or trending data 104, 104f (where p (t) is the recorded PA pressure after implant and estimated parameters $p_0$, $p_\infty$, and $\alpha$ denote the baseline PA pressure before implant, final steady state or stable period PA pressure, and time constant, where 1/time constant or $1/\alpha$ is time in days after implant from a transient period to a stable period, respectively), as discussed in more detail below. The regression model $p(t)=p_\infty+e^{-\alpha t}(p_0-p_\infty)$ is one example of a model that may be used. In other embodiments, other models, logistic or similar curves, may be used or applied with the embodiments described herein. For example, linear or sigmoidal-type regression models may be used.

The method 100a may further include determining (e.g., computing or calculating) deviation(s) (e.g., $\Delta_p$, $\Delta_\alpha$) between at least one of the estimated parameters (e.g., $p_\infty$, $1/\alpha$) and at least one of ideal parameters (e.g., $p_{\infty,ideal}$, $1/\alpha_{ideal}$) 106, 106f. The estimated parameters are computed from the regression model as applied to the received plurality of PA pressure measurements or PA pressure trending data. For example, (e.g., $p_\infty$, $1/\alpha$) are estimated from the regression model (e.g., by maximizing likelihood or minimizing L2 error). Values for the ideal parameters can be computed by fitting the regression model to the PA pressure trend data or measurements from a patient population (e.g., historical data from a patient population) that responded well following implant of an LVAD, as discussed in more detail below. In other embodiments, ideal parameters may be estimated directly from historical patient population data without fitting or applying a regression model (e.g., from mean stabilization period pressure data) to the historical patient population data. The ideal parameters or threshold values as described herein may be stored in, for example, a database, computer memory, or look up table that may be accessible by a clinician, patient, processor, controller, or other computing device.

In some embodiments, the method 100a includes adjusting at least one operating parameter of a blood pump based on the determined deviation 108a. Adjusting at least one operating parameter of the blood pump may include adjusting one or more of: a pumping speed, flow rate (e.g., increasing or decreasing flow rate), or a pumping operation mode (e.g., pulsatile or continuous mode) based on the calculated or computed deviations to optimize LVAD therapy 110, 110f (e.g., prevent onset or worsening of RHF). In some embodiments, adjusting one pumping parameter may adjust another parameter. For example, adjusting flow rate may adjust pumping speed and vice versa. Examples of pump operating parameters and adjustment that can be included in the present application are described in U.S. Pat. No. 8,506,471, the contents of which is incorporated herein by reference in its entirety. For example, method 100a may include a step of determining if the deviation exceeds a threshold value as described below, and increasing the flow rate if the deviation exceeds the threshold value 110. The method 100a may include a step of determining if the deviation is less than the threshold value as described below, and decreasing the flow rate if the deviation is less than the threshold 111. Further, in some embodiments, a method may include determining if a deviation falls within certain thresholds and not adjusting an operating parameter of the pump if the deviation falls within the thresholds, if for example, the patient is identified as being responsive to LVAD therapy or not at risk for RHF (see FIG. 1C). A controller or other computing device may be provided to adjust the operating parameter as described in more detail below.

Figure 1B:
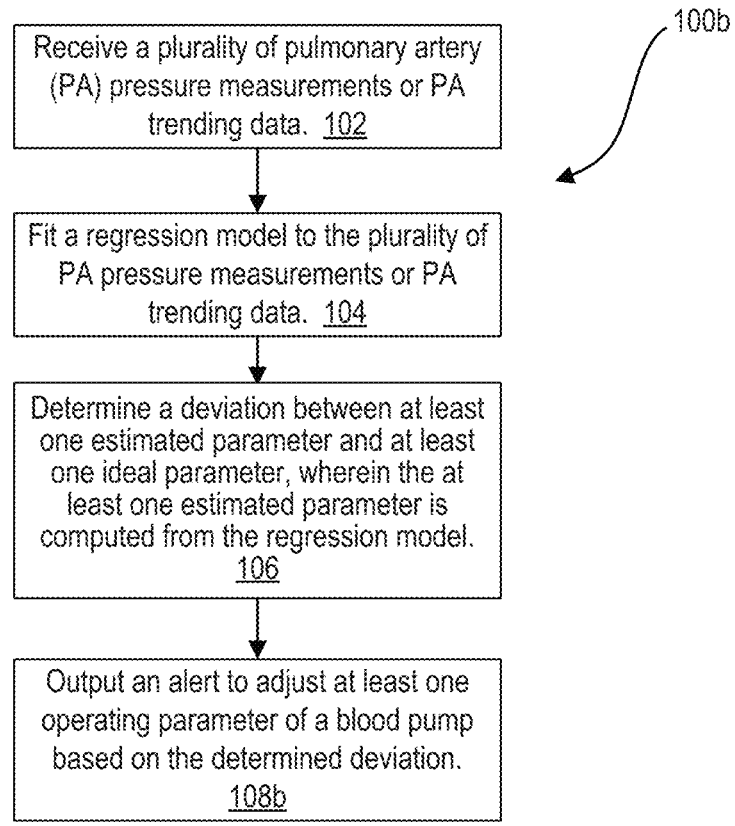

In some embodiments, as illustrated in FIG. 1B, an exemplary method 100b may include outputting an alert (e.g., to a clinician) to adjust an operating parameter of the pump or to identify that the patient is at risk for onset or worsening RHF 108b. For example, if the determined deviations are greater than or less than certain threshold values as described in more detail below, the method may include outputting such an alert. This alert or notification may occur prior to adjusting the at least one operating parameter of the blood pump in step 108a of method 100a. In some embodiments, a clinician adjusts the operating parameter in response to the alert. In other embodiments, a controller or other computing device is configured to adjust the operating parameter in response to the alert. Further, in some embodiments, the alert or notification includes a visual, audio, or haptic alert.

Figure 1C:
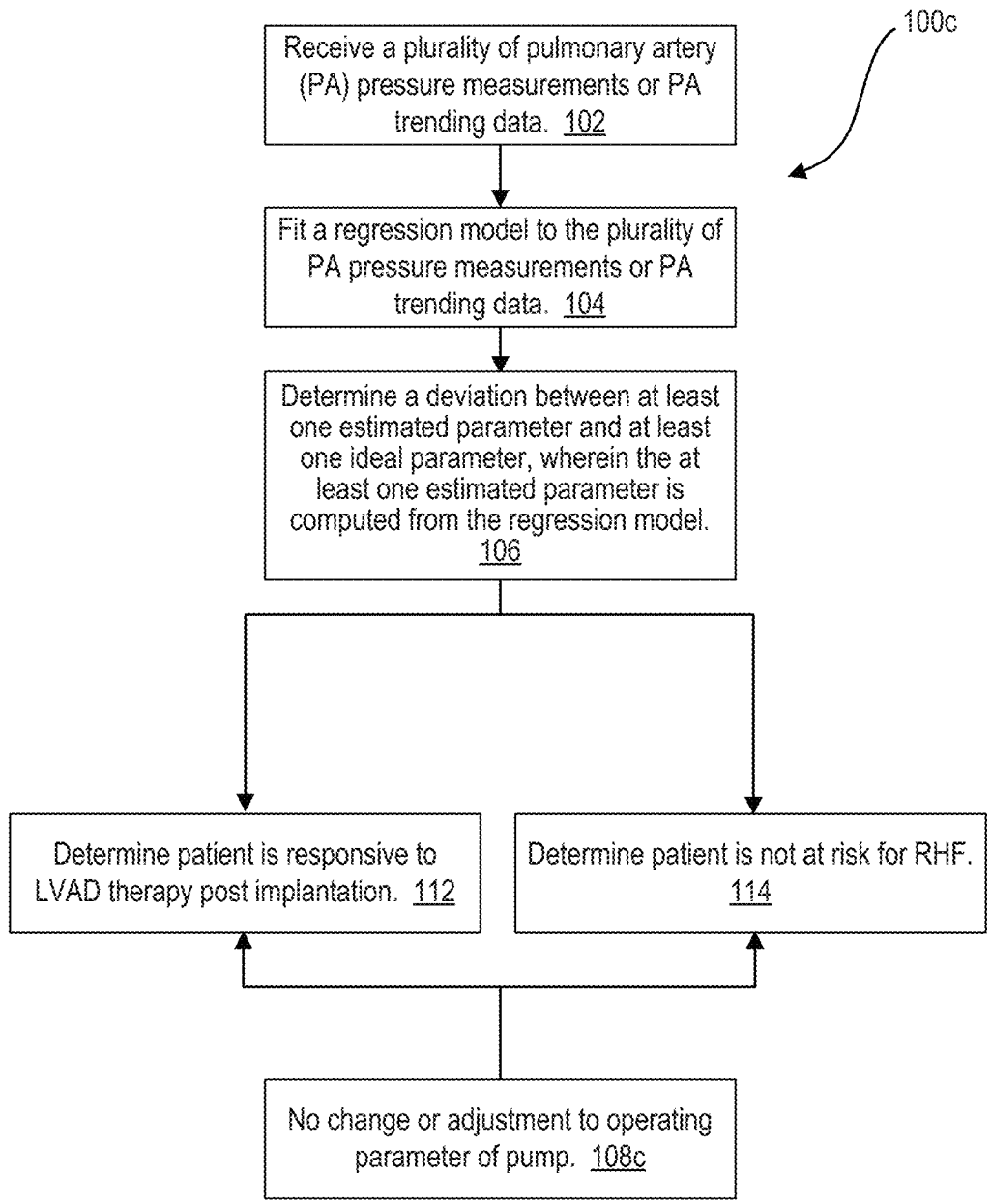

As illustrated in FIG. 1C, an exemplary method 100c may include determining whether a patient is responsive to LVAD therapy post implantation 112 or be identified as not at risk for RHF 114 based on the determined deviation (e.g., step 106) if the deviation falls within certain threshold values as discussed in more detail below. If it is determined that the patient is responsive to LVAD therapy post implantation or is identified as not at risk for RHF, then no change or adjustment to the operating parameter of the blood pump is made 108c.

Figure 1D:
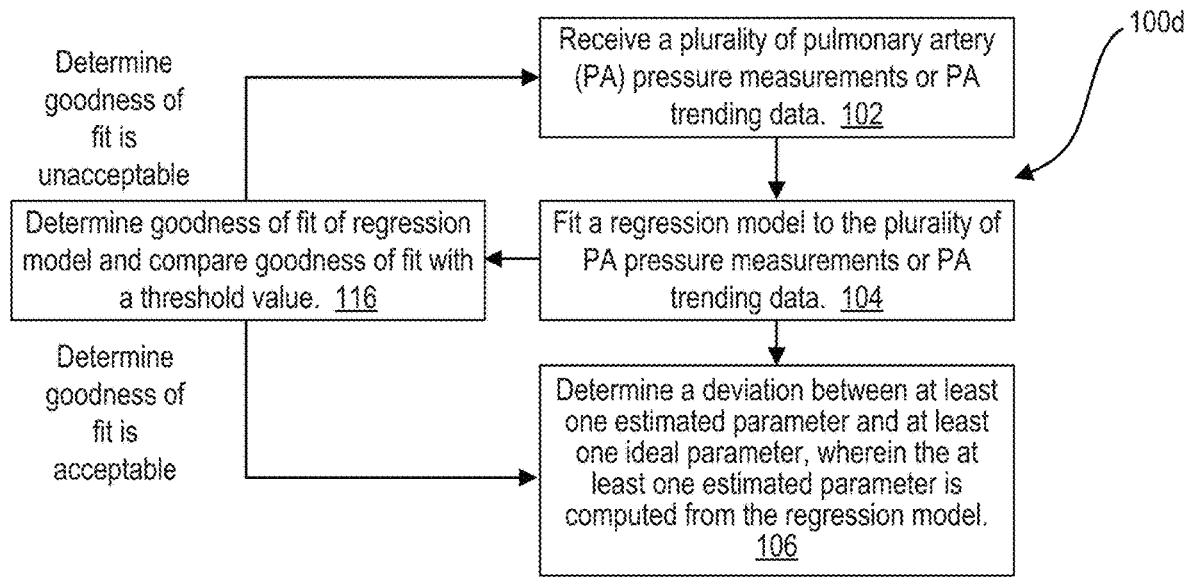

With reference to FIG. 1D, an exemplary method 100d may include determining a goodness of fit (e.g., variability or goodness of fit error) of the regression model and comparing the goodness of fit to an acceptable threshold value 116, 116f. The goodness of fit is determined prior to determining a deviation between estimated and ideal parameters (e.g., step 106). The goodness of fit of the regression model refers to the extent to which observed data fits or corresponds to the data from the assumed model (e.g., how well the PA pressure measurements or trend data fit the regression or assumed model). For example, if the goodness of fit is greater than the acceptable threshold value (e.g., variability is unacceptable), more data is collected (e.g., steps 102, 104, and 116 may be repeated) until the goodness of fit is less than the acceptable threshold (e.g., variability is acceptable). In some embodiments, a clinician may be notified or informed to wait for or receive more pressure measurements. If the goodness of fit is less than the acceptable threshold, the method may proceed to the step of determining the deviation between estimated and ideal parameters (e.g., step 106) and subsequent other steps (e.g., one or more of steps 108a-114).

Figure 1E:
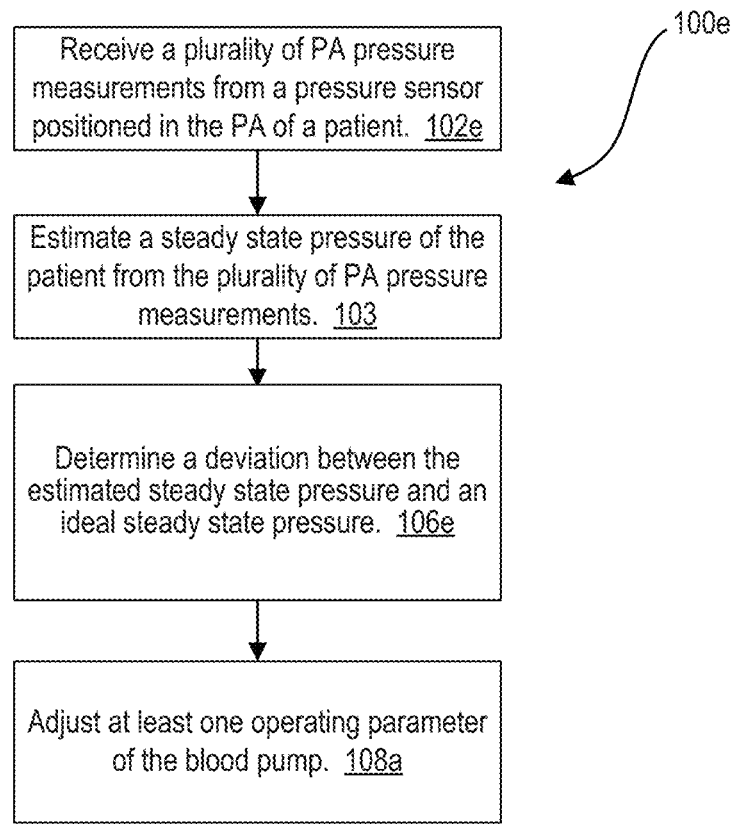

With reference to FIG. 1E, an exemplary method 100e may include receiving a plurality of PA pressure measurements from a pressure sensor positioned in the PA of a patient 102e, estimating a steady state pressure of the patient from the plurality of PA pressure measurements 103, determining a deviation between the estimated steady state pressure and an ideal steady state pressure 106e, and adjusting at least one operating parameter of a blood pump based on the determined deviation 108.

Figure 1F:
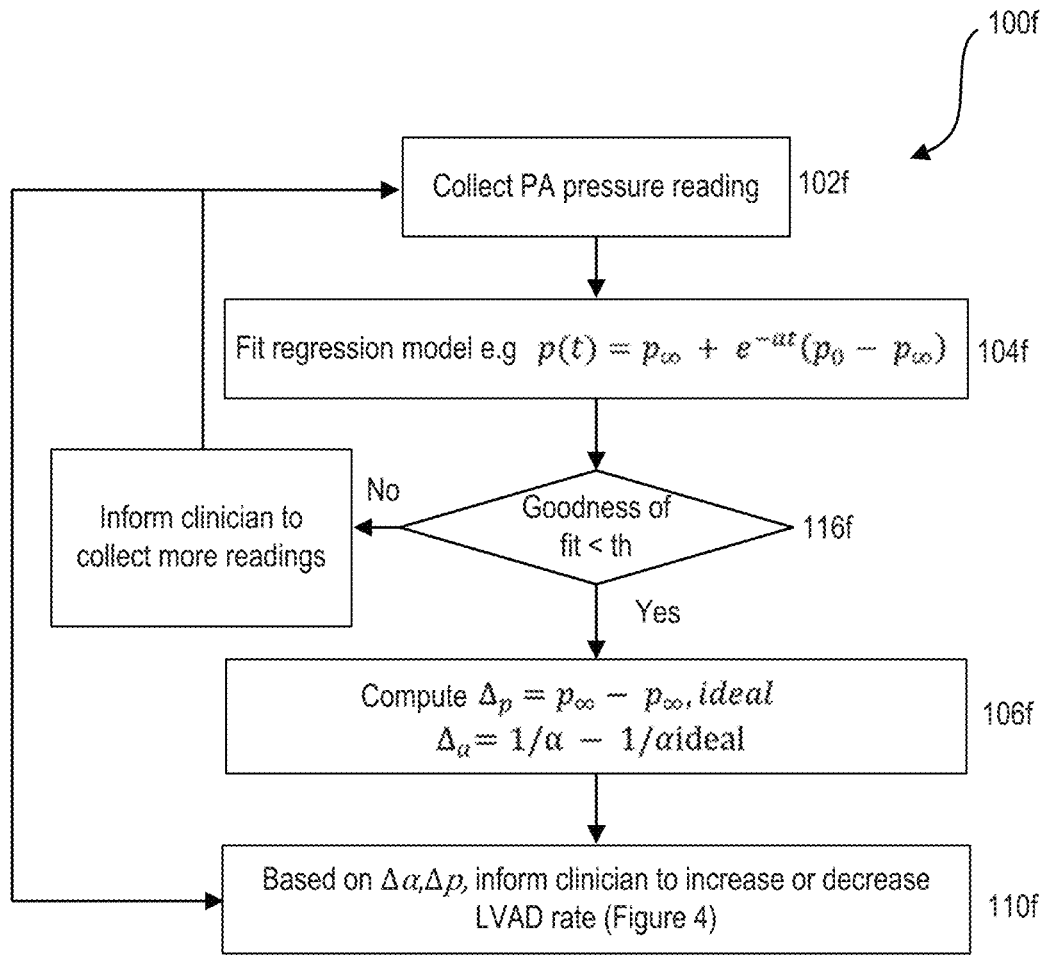

With reference to FIG. 1F, another exemplary method 100f is illustrated configured in accordance with the embodiments described herein. Any of the steps of methods 100a-100f described above may be repeated to identify whether further adjustment, goodness of fit, PA pressure measurements or trend data is required. As such, method 100 may be an iterative process with one or more steps repeated as necessary. In some embodiments, the methods 100a-100f may include alerting or informing the clinician to adjust the pumping operation based on a comparison between the calculated deviations and a lookup table or database (e.g., of deviation thresholds calculated from a patient population with known flow rates and responses), as discussed in more detail below. In other embodiments, the methods may include alerting or informing the clinician to change or adjust medications (e.g., diuretics, inotropes) based on the calculated or computed deviations instead of or in addition to adjusting the pumping operation of the LVAD. While the embodiments herein may refer to identifying, notifying or adjusting, by a clinician, any of the embodiments may include identifying, notifying, or adjusting by a patient instead of or in addition to the clinician. Further, in some embodiments a controller or other suitable computing device is configured to implement any of the steps described herein (e.g., in methods 100a-100f) instead of or in addition to the patient or clinician as described in more detail below. While referring specifically to PA pressure data or measurements, in other embodiments, other data in addition to or in combination with PA pressure may be received, collected, compared, or evaluated to determine whether to adjust an operating parameter of a blood pump to reduce onset of RHF. Such other data or measurements may include heart rate, diastolic or systolic right heart volume, or ejection fraction.

Figure 2:
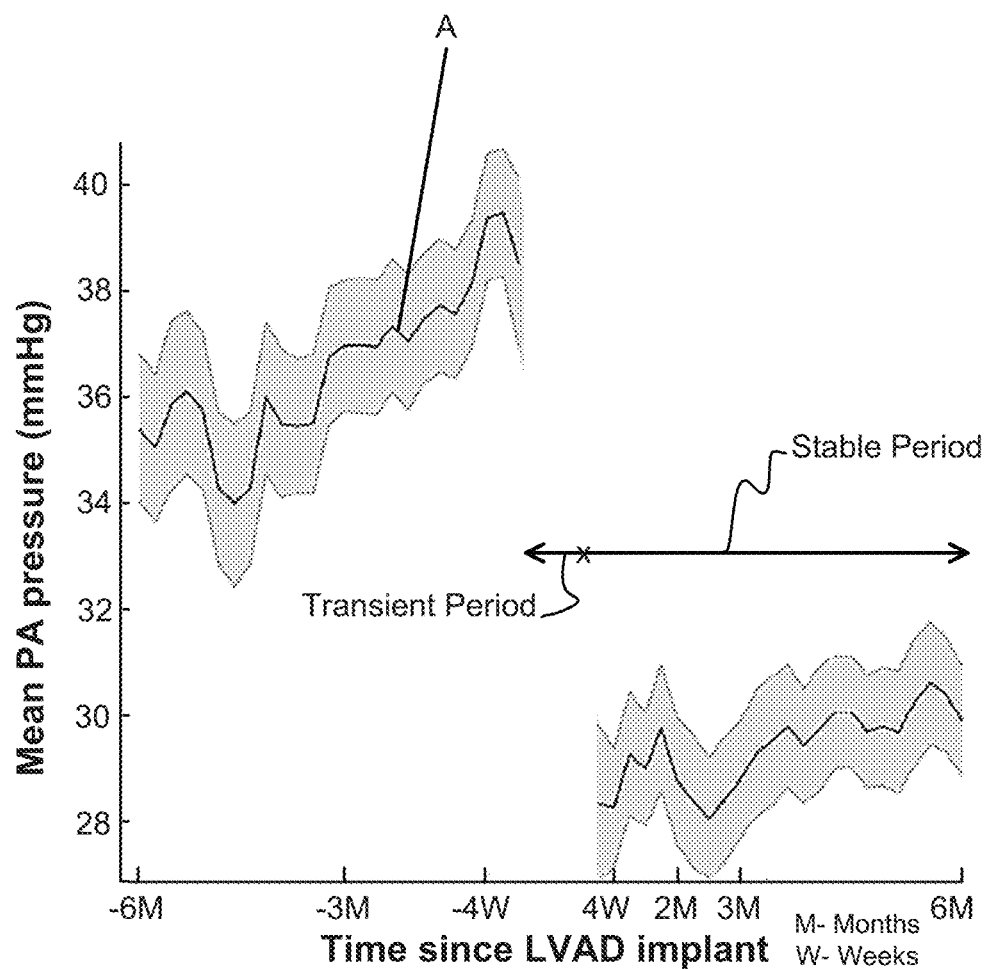
FIG. 2 illustrates an exemplary Mean PA Pressure-Time graph of historical patient data pre- and post-LVAD implant according to some embodiments as described herein.

FIG. 2 illustrates an exemplary graph of "Mean PA Pressure vs. Time" of historical patient data pre- and post-LVAD implant. Curve "A" represents an average of the historical data points (e.g., shown in gray). As shown, PA pressures tend to decrease substantially within a couple weeks following implantation of the LVAD and stabilize or plateau onto a lower value compared to pre-LVAD implant levels. The first period of time when PA pressures tend to decrease substantially following implant may be referred to herein and identified in FIG. 2 as a "transient period". The second period of time after the transient period when PA pressures stabilize or plateau may be referred to herein and is identified as a "stable period". Although the PA pressure measurements, trending data, and curves are described in terms of mean PA pressure, diastolic or systolic PA pressure measurements or curves may also be used in the embodiments described herein.

Patients may show different transient period durations and different PA pressures in the stable period following LVAD implant. Differences in transient period duration or PA pressures in the stable period may be correlated to LVAD flow rates, and may also be used as a surrogate or proxy for a patient's right heart status or responsiveness to LVAD therapy. For example, LVAD patients for whom PA pressures stabilized within a pre-determined target zone (e.g., about 15 to about 35 mmHG) or within a designated time zone (e.g., less than about 15 to 20 days) may have a reduced risk of RHF and associated mortality compared to those patients for whom the PA pressures have not stabilized within the designated time period or have stabilized outside of the predetermined target zone.

The transient and stable periods for each patient following LVAD implant may be identified as disclosed herein. Further, based on PA pressure measurements (e.g., received from a PA sensor during the transient period, stable period, or both), a clinician may be notified of or alerted to a patient's status as to whether the patient has stabilized or appears to be stabilizing into a high, medium, or low PA pressure range. For example, patients who stabilize or appear to be stabilizing into particularly high stabilization PA pressures (e.g., greater than about 35 mmHG) may indicate high afterload on a right ventricle of the patient, which may accelerate RHF in the patient. Adjusting a pump operating parameter or LVAD therapy (e.g., by increasing LVAD flow rate) may relieve the increased afterload on the patient's right ventricle and prevent onset or worsening of RHF as discussed below. Conversely, low stabilization PA pressures (e.g., less than about 15 mmHG) may indicate an inability of the right ventricle to respond to increased flow due to the implanted LVAD. Decreasing flow rate in this context may be helpful to prevent onset or worsening of RHF. As such, patients at risk for onset or worsening of RHF may be identified, clinicians informed or alerted, and pump operating parameters or LVAD therapy adjusted accordingly to optimize treatment and improve patient outcomes, as discussed in more detail below. In some embodiments, non-responsive patients may also be identified (e.g., if time to stabilization is either too short or too long relative to an ideal time constant or period). Further, in some embodiments, patients responsive to LVAD therapy or not at risk of RHF may be identified, where no adjustment of pump operating parameters or LVAD therapy is necessitated. In such embodiments, the patient may continue to be monitored to see if adjustment of pump operating parameters or LVAD therapy is necessitated at a later time.

Figure 3:
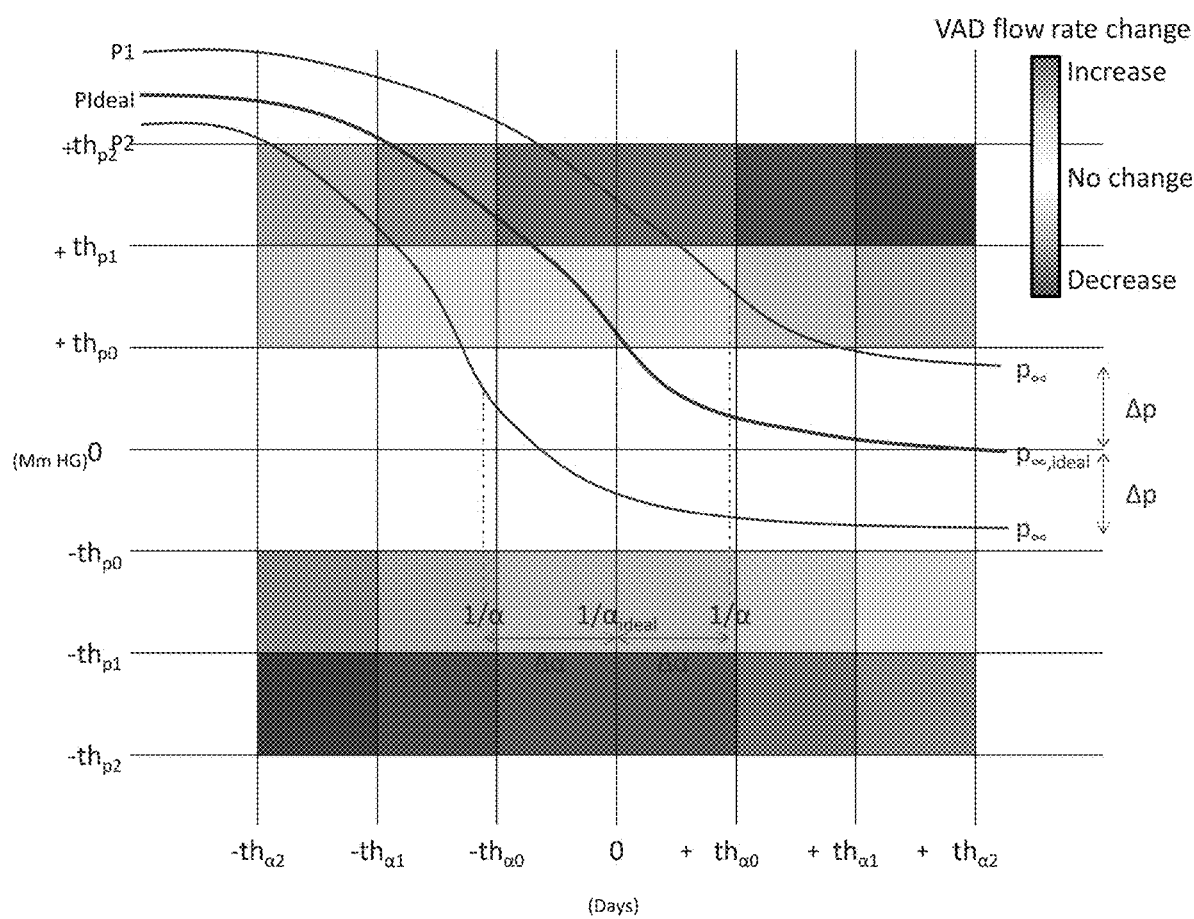
FIG. 3 illustrates exemplary patient and ideal PA Pressure curves and corresponding thresholds according to embodiments as described herein.

With reference to FIG. 3, an ideal PA pressure profile or curve (e.g., identified as PIdeal) is shown. As discussed above, the ideal PA pressure curve may be derived from fitting regression model (e.g., $p(t)=p_\infty+e^{-\alpha t}(p_0-p_\infty)$) or other suitable logistic or similar curve to historical data (e.g., using collected PA pressure data during the transient period, stable period, or both) of patients that responded well following LVAD implant. Ideal parameters (e.g., $p_{\infty,ideal}$, $1/\alpha_{ideal}$) may then be estimated from the regression model. In some embodiments, $p_{\infty,ideal}$ (e.g., an ideal steady state pressure in the stable period) may be between about 15-35 mmHG, about 20-25 mmHG, about 20 mmHG, about 25 mm HG, or other values as determined. In some embodiments, $1/\alpha_{ideal}$ (e.g., an ideal length of the transient period or the time at which the transient period transitions to the stable period) may be between about 0 to 5 days, about 0 to 7 days, about 5 to 10 days, about 10 to 15 days, or about 15 to 20 days. In other embodiments, $1/\alpha_{ideal}$ may be less than about 20 days, less than about 15 days, less than about 10 days, less than about 5 days, or other values as determined.

As discussed above, based on a comparison (e.g., determined deviations $\Delta_p$, $\Delta_\alpha$) between the estimated parameters of a patient's PA pressure curve and an ideal PA pressure curve, the clinician may balance or be notified to balance the patient's preload and afterload (e.g., by adjusting pumping operation parameter of the LVAD or medications administered to the patient) to prevent onset or worsening of RHF in the patient. For example, the clinician may adjust (e.g., increase or decrease) flow rate of the LVAD to keep or maintain estimated parameters $p_\infty$, $1/\alpha$ of a patient within a desirable range of ideal parameters $p_{\infty,ideal}$, $1/\alpha_{ideal}$ (e.g., as discussed in more detail below with reference to FIG. 3). In some embodiments, flow rate is adjusted to keep or maintain both $p_\infty$, $1/\alpha$ within a desirable range of $p_{\infty,ideal}$, $1/\alpha_{ideal}$. In other embodiments, flow rate is adjusted to keep or maintain only $p_\infty$ within a desirable range of $p_{\infty,ideal}$ as preventing RHF may be primarily dependent on maintaining estimated steady state or stable period PA pressure within an ideal PA pressure range. In yet other embodiments, flow rate is adjusted to keep or maintain only $1/\alpha$ within a desirable range of $1/\alpha_{ideal}$ as preventing RHF may be primarily dependent on maintaining an estimated transient period duration within a designated time period. In some embodiments, actual measured steady state or stable period pressure or time constant of a patient can be collected or received and compared to ideal parameters (e.g., as described above) and a pump operation parameter adjusted to prevent onset or worsening of RHF in the patient As illustrated in FIG. 3, LVAD flow rates may be increased or decreased based on the determined deviations $\Delta_p$, $\Delta_\alpha$ between the estimated parameters $p_\infty$, $1/\alpha$ of a patient's PA pressure curve (e.g., two different patient curves are identified as P1 and P2, respectively) and the estimated ideal parameters $p_{\infty,ideal}$, $1/\alpha_{ideal}$ of the ideal PA pressure curve (e.g., identified as PIdeal). As described above with respect to methods 100a-100f, a patient's estimated PA pressure curve may be derived by fitting a regression model (e.g., $p(t)=p_\infty+e^{-\alpha t}(p_0-p_\infty)$) or other suitable logistic or similar curve to the patient's received PA pressure measurements (e.g., during the transient period after implant). A goodness of fit of the regression model is obtained and compared to a goodness of fit threshold. Parameters $p_\infty$, $1/\alpha$ may then be estimated from the regression model if the goodness of fit is less than the threshold. In some embodiments, mean squared error (MSE) between model estimated pressure values $\hat{p}_i$ and observed pressure values $p_i$ may be computed for n available pressure readings using:

$$\frac{1}{n}\sum_{i=1}^{n}(\hat{p}_i - p_i)^2 \qquad \text{(Equation 1)}$$

to obtain goodness of fit. For example, if MSE is greater than 25 (e.g., an acceptable threshold), the goodness of fit is greater than an acceptable threshold. If MSE is less than 25, the goodness of fit is acceptable or less than an acceptable threshold. While MSE may be used to obtain goodness of fit, other ways may also be used to evaluate goodness of fit or likelihood which may have their own different threshold values (e.g., Akaike information criterion, Bayesian information criterion). In some embodiments, MSE may be applied to an unseen validation error.

Deviations $\Delta_p=p_\infty-p_{\infty,ideal}$, $\Delta_\alpha=1/\alpha-1/\alpha_{ideal}$ are then determined by comparing the estimated parameters of the respective curves with the ideal curve (e.g., between PIdeal and P1 or PIdeal and P2). Deviation threshold values (e.g., $\pm th_{p0}$, $\pm th_{p1}$, $\pm th_{p2}$, $\pm th_{\alpha 0}$, $\pm th_{\alpha 1}$, $\pm th_{\alpha 2}$) between the estimated parameters of a patient's PA pressure curve and an ideal PA pressure curve may be used to determine whether a pump operating parameter (e.g., LVAD flow rate) is increased or decreased and subsequently, relative rates of increase or decrease, as discussed below. The deviation threshold values may also be determined or set by historical data of known flow rates and responses of patients following LVAD implant. For example, in some embodiments as discussed above, an ideal stable period or steady state pressure $p_{\infty,ideal}$ may be determined to be between about 15-35 mmHG. Therefore, if the ideal steady state pressure $p_{\infty,ideal}$ is set to about 25 mmHG (e.g., corresponding to "0" on the Y-axis), threshold values $\pm th_{p0}$ may then be set to, for example, about 10 mmHG (e.g., such that $+th_{p0}$ is about 35 mm HG and $-th_{p0}$ is about 15 mm HG, respectively).

Threshold values $\pm\text{th}_{p1}$ may then be set nominally to another about 5 mmHG, about 10 mmHG, or another suitable value from $\pm\text{th}_{p0}$. Similarly, threshold values $\pm\text{th}_{p2}$ may also be set nominally to another about 5 mmHG, about 10 mmHG, or another suitable value from $\pm\text{th}_{p1}$. Threshold values, $\pm\text{th}_{\alpha0}$, $\pm\text{th}_{\alpha1}$, $\pm\text{th}_{\alpha2}$ may be determined or established in a similar manner. For example, ideal time constant or time when the transient period transitions to the stable period (e.g., as discussed above), $1/\alpha_{ideal}$, may be set based on historical data (e.g., to about 15 days corresponding to "0" on the X-axis). The threshold values $\pm\text{th}_{\alpha0}$, $\pm\text{th}_{\alpha1}$, $\pm\text{th}_{\alpha2}$ may then be set based off $1/\alpha_{ideal}$.

In the illustrated embodiment of FIG. 3, both patient PA pressure curves P1 and P2 have deviations $\Delta_p$ that fall within thresholds $\pm\text{th}_{p0}$. As shown, in some embodiments, when deviation $\Delta_p$ is within certain thresholds (e.g., $-\text{th}_{p0}<\Delta_p<\text{th}_{p0}$), LVAD flow rate adjustment or other pump operating parameter may not be necessary or required. In other words, the patient may be responding adequately following LVAD implant or is not at risk of RHF and adjustment is not necessary to prevent onset or worsening of RHF. Also, in such embodiments, LVAD adjustment or status of the patient following implant may be primarily dependent on the deviation $\Delta_p$. Regardless of the deviation $\Delta_\alpha$, adjusting LVAD therapy may not be necessary because deviation $\Delta_p$ is within certain thresholds.

In other embodiments, deviation $\Delta_p$ is within certain thresholds that may require increasing LVAD flow rate or other pump operating parameter. The relative amount (e.g., level) of increase in flow rate may depend on or be governed by one or both values of deviations $\Delta_p$, $\Delta_\alpha$. For example, as illustrated in FIG. 3, in some embodiments, deviation $\Delta_p$ may be between threshold values (e.g., $+\text{th}_{p0}\leq\Delta_p\leq+\text{th}_{p2}$). As discussed above, particularly high stabilization PA pressures (e.g., greater than about 35 mmHG) may indicate high afterload on a right ventricle of the patient, which may accelerate RHF in the patient. Adjusting a pump operating parameter or LVAD therapy (e.g., by increasing LVAD flow rate) may relieve increased afterload on the patient's right ventricle and prevent onset or worsening of RHF when deviation $\Delta_p$ falls within such thresholds. However, a larger relative increase in flow rate may be required for a deviation $\Delta_p$ between threshold values (e.g., $+\text{th}_{p1}\leq\Delta_p\leq+\text{th}_{p2}$) relative to a deviation $\Delta_p$ between thresholds (e.g., $+\text{th}_{p0}\leq\Delta_p<+\text{th}_{p1}$) as illustrated in FIG. 3 and the corresponding table of FIG. 4 showing relative change in flow rates based on deviations $\Delta_p$, $\Delta_\alpha$ and deviation threshold values. Thus, increases in deviation $\Delta_p$ may correspond to larger relative increases in LVAD flow rate. Further, in some embodiments, relative increase in flow rates may also depend on deviation $\Delta_\alpha$. As illustrated, when deviation $\Delta_\alpha$ increases, a relative decrease in flow rate may also be required. For example, a smaller relative increase in flow rate may be required for a deviation $\Delta_p$ (e.g., $+\text{th}_{p1}\leq\Delta_p\leq+\text{th}_{p2}$) and a deviation $\Delta_\alpha$ between threshold values (e.g., $+\text{th}_{\alpha1}\leq\Delta_\alpha\leq+\text{th}_{\alpha2}$) relative to a deviation $\Delta_\alpha$ between threshold values (e.g., $+\text{th}_{\alpha0}\leq\Delta_\alpha<+\text{th}_{\alpha1}$).

In other embodiments, deviation $\Delta_p$ is within certain threshold values that may require decreasing LVAD flow rate or other pump operating parameter. The relative amount of decrease in flow rate may depend on or be governed by one or both values of deviations $\Delta_p$, $\Delta_\alpha$. For example, as illustrated in FIG. 3, in some embodiments, deviation $\Delta_p$ may be between threshold values (e.g., $-\text{th}_{p2}\leq\Delta_p\leq-\text{th}_{p0}$). As discussed above, low stabilization PA pressures (e.g., less than about 15 mmHG) may indicate an inability of the right ventricle to respond to increased flow due to the implanted LVAD. Adjusting LVAD therapy by decreasing flow rate may be helpful to prevent onset or worsening of RHF when deviation $\Delta_p$ falls within such threshold values. However, a larger relative decrease in flow rate may be required for a deviation $\Delta_p$ between threshold values (e.g., $-\text{th}_{p2}\leq\Delta_p\leq-\text{th}_{p1}$) relative to a deviation $\Delta_p$ between threshold values (e.g., $-\text{th}_{p1}<\Delta_p\leq-\text{th}_{p0}$) as illustrated in FIG. 3 and the corresponding table of FIG. 4. Further, in some embodiments, relative decrease in flow rate may also depend on deviation $\Delta_\alpha$. For example, a smaller relative decrease in flow rate may be required for a deviation $\Delta_p$ (e.g., $-\text{th}_{p2}\leq\Delta_p\leq-\text{th}_{p1}$) and a deviation $\Delta_\alpha$ between thresholds (e.g., $-\text{th}_{\alpha2}\leq\Delta_\alpha\leq-\text{th}_{\alpha1}$) relative to a deviation $\Delta_\alpha$ between thresholds (e.g., $-\text{th}_{\alpha1}<\Delta_\alpha\leq-\text{th}_{\alpha0}$).

Figure 5:
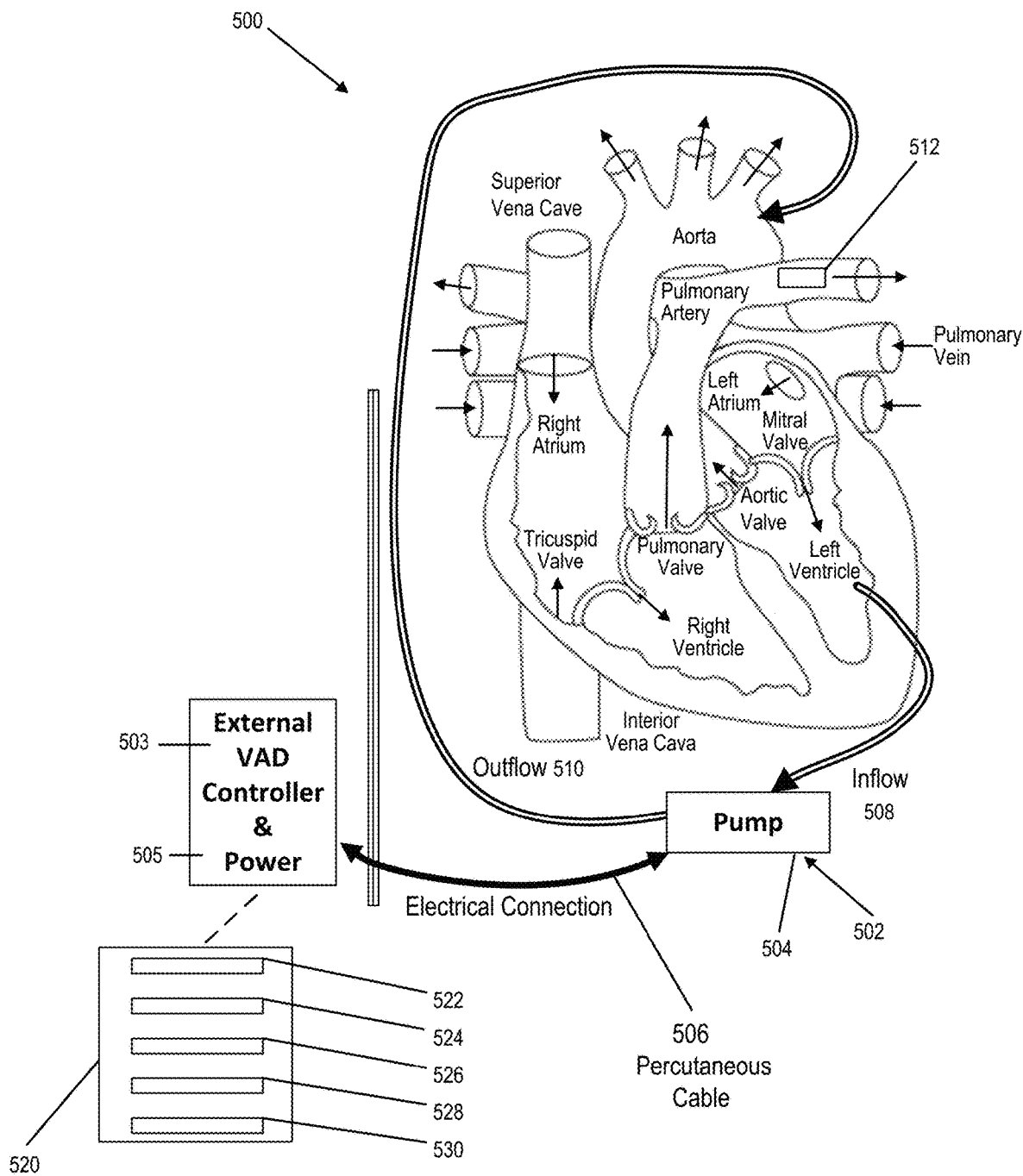
FIG. 5 illustrates an exemplary blood pump system according to some embodiments as described herein.

FIG. 5 illustrates an exemplary blood pump system 500 according to some embodiments that may be configured to carry out any steps of methods 100a-100f of FIGS. 1A-1F (e.g., to receive patient PA pressure measurements or trending data, identify or alert a clinician of a patient at risk of onset or worsening RHF, determine deviations, apply or fit regression models, determine goodness of fit, adjust a pump operating parameter or LVAD therapy to prevent onset or worsening of RHF, or determine a patient is not at risk of RHF or is responsive to LVAD therapy. Blood pump system 500 includes a left ventricular blood pump 502 and a controller 503 operably coupled to the pump. In some embodiments, the pump 502 can be configured similar to an LVAD described in U.S. Patent Publication 2015/0290374; U.S. Patent Publication 2014/0188148; U.S. Pat. Nos. 9,091, 271; 8,794,989, 8,682,431; and/or 8,894,561, the contents of which are incorporated herein by reference in their entireties. The blood pump 502 includes a housing 504. Housing 504 encloses a motor and rotor. Pump 502 and controller 503 may be powered by a power supply 505 (e.g., a battery).

Controller 503 may be an external controller (e.g., coupled to the blood pump 502 by a percutaneous cable 506, wirelessly, or the like) or an implantable, on-board controller of blood pump 502. In some embodiments, controller 503 may be a separate external or implantable computing device (e.g., mobile tablet, laptop, mobile phone, desktop). In some embodiments, controller 503 include two or more control units (e.g., external, implanted, or both). In some embodiments, the pump 502 may include an inflow 508 coupled to a chamber of the heart (illustrated as the left ventricle, but other chambers may be cannulated by inflow 508) and an outflow 510. The blood pump system 500 further includes one or more implantable cardiac electronic devices (e.g., pressure sensors 512) configured to be implanted within the PA of the patient to collect, receive, or transmit PA pressure measurements (e.g., readings, signals). The PA pressure sensor may be automatically (e.g., programmed) or manually interrogated to collect PA pressure measurements or PA trending data. The PA pressure sensor may transmit (e.g., wired or wirelessly) the PA pressure data to an interrogation unit, the controller, or other computing device as discussed in more detail below.

Many traditional sensors can be used, including MEMS, strain gauges, piezo-based sensors, capacitive sensors, transonic, ultrasound Doppler, or the like. U.S. Pat. No. 6,855, 115, U.S. Provisional Patent Application 62/194,700, and U.S. Provisional Patent Application 62/194,608 describe pressure sensor configurations, interrogation units, and pressure sensing methods that may be utilized in any of the embodiments of the present disclosure. The contents of each provisional patent application and patent are incorporated herein in their entireties for all purposes.

The system 500 may include an external interrogation circuit or unit 520 configured to interrogate pressure sensor 512 for PA pressure measurements. The pressure sensor 512 may be operably coupled (wired or wirelessly) with interrogation unit 520. In some embodiments, the interrogation unit 520 is a hand-held unit. The interrogation unit 520 may include a transceiver 522, an antenna 524, and a microprocessor 526 for generating, receiving, and analyzing signals (e.g., PA pressure measurements) from sensor 512 as discussed in more detail below. The antenna 524 may be integrated within a housing of the interrogation unit 520 or may be detachable such that it may be positioned on a patient's body in proximity to sensor 512. The interrogation unit 520 may include a power supply 528 configured to provide power to the unit 520 or may be operably coupled to the power supply 505 of the pump 502 or controller 503. In some embodiments, the interrogation unit 520 is integrated with the controller 503. In some embodiments, the interrogation unit 520 is electronically coupled to the controller 503 wirelessly or by wires.

In use, the antenna 524 of the interrogation unit 520 may be used to interrogate sensor 512 (e.g., generate and receive signals from the sensor 512). In such embodiments, the sensor 512 may be a passive sensor without a battery or other power source. In other embodiments, the sensor 512 includes a battery or other power source and actively sends PA signals to the interrogation unit 520. In some embodiments, the interrogation unit 520 is programmed to interrogate sensor 512 at pre-set intervals during a transient period following LVAD implant (e.g., multiple times a day for about 15-20 days) to collect or receive desired PA pressure measurements according to method 100. In other embodiments, a patient or clinician may manually operate the interrogation unit 512 to collect or receive such PA pressure measurements according to a pre-determined schedule from the pressure sensor 512.

In some embodiments, the interrogation unit 520 may be programmed to analyze or process the collected PA pressure measurements (e.g., fit a regression model, determine goodness of fit, estimate a PA pressure curve and associated parameters, calculate deviations, compare deviations with thresholds). The interrogation unit 520 may send the measurements to the controller 503 to perform the data analysis. In other embodiments, a clinician or patient may perform (e.g., manually) one or more of any of the method steps as discussed above (e.g., fitting a regression model, determining goodness of fit, estimating a PA pressure curve and associated parameters, calculating deviations, comparing deviations with thresholds). As discussed above, PA pressure measurements or data may serve as a proxy for the patient's right heart status. The interrogation unit 520, separate or integrated controller (e.g., controller 503), patient, or clinician may then adjust flow rate or other pump parameter of the blood pump 502 in response to the PA pressure measurements and analysis. For example, based on deviations $\Delta_p$, $\Delta_\alpha$ between the estimated parameters $p_\infty$, $\alpha$ from a PA measurement curve of a patient and estimated parameters $p_{\infty,ideal}$, $\alpha_{ideal}$, from an ideal PA measurement curve derived from historical data of previous patients, a flow rate or other operating parameter of the blood pump 502 may be adjusted (e.g., increased or decreased) to prevent RHF as discussed above.

In some embodiments, the interrogation unit 520 includes a display 530 configured to display one or more of the PA pressure measurements, PA pressure curves, goodness of fit, estimated parameters, calculated deviations, or amount of required flow rate adjustment. In some embodiments, the interrogation unit 520 may also be configured to identify or alert a clinician or patient that a patient is at risk of RHF or to inform or recommend that the LVAD flow rate should be adjusted (e.g., via the display, or with a visual, haptic, or audible signal). In other embodiments, data or signals (e.g., PA pressure measurements or other info) from the interrogation unit 520 may be transferred or uploaded to a separate computing device (e.g., desktop, laptop, micro-PC, mobile phone, mobile tablet, controller 203) for further review, analysis, or processing (e.g., fit a regression model, determine goodness of fit, estimate a PA pressure curve and associated parameters, calculate deviations, compare deviations with thresholds). Data, alerts, or recommendations may also be displayed on a separate display or monitor (e.g., of the separate computing device) for viewing or analysis by a patient or clinician. The clinician, patient, interrogation unit, or separate computing device may access historical data of ideal parameters or thresholds from a database or lookup table for review, analysis, or processing. In some embodiments, the interrogation unit, or separate computing device may include memory for storing such information.

In certain embodiments, the interrogation unit 520 or pressure sensor 512 may be integrated or operably coupled to the pump 502 or external controller 503. As discussed above, for example, the interrogation unit 520 may be powered by the power supply 505 of the pump 502 and controller 503. In some embodiments, data, alerts, or recommendations may be transmitted to and displayed on a display of the controller 503 directly from the interrogation unit 520 or indirectly from an intermediate device (e.g., second controller or other computing device). In some embodiments, the interrogation unit 520 is housed in a same housing as the external controller 503.

In some embodiments, the interrogation unit 520 or pressure sensor 512 may be integrated or operably coupled with the pump 502 or external controller 503 such that a closed-loop system is provided. For example, the blood pump system 500 may be programmed or set to adjust flow rate of the LVAD as necessary to prevent onset or worsening of RHF following implant. The interrogation unit 520 may interrogate the sensor 512 to generate and receive PA pressure measurements according to a pre-determined or pre-programmed schedule. The interrogation unit 520 may then process or analyze the PA pressure measurements as described herein and instruct the controller 503 to adjust the flow rate or other operating parameter of the pump 502 based on the PA pressure measurements and analysis as discussed above. The process may then be repeated until further LVAD flow rate is not required or a patient is not at risk of RHF. In other embodiments, the PA pressure measurements may be sent or uploaded to the controller 503 or other separate computing device for processing.

In some embodiments, the controller 503 may be configured to carry out any of the steps as described above with respect to methods described herein. For example, the controller 503 may be configured to receive a plurality of pulmonary artery (PA) pressure measurements or PA trending data from an implantable cardiac electronic device; fit a regression model to the plurality of PA pressure measurements or PA trending data; determine a deviation between at least one estimated parameter and at least one ideal parameter, wherein the at least one estimated parameter is computed from the regression model; or adjust at least one operating parameter of the blood pump based on the determined deviation. The controller 503 may be integrated with the interrogation unit as discussed above. In other embodiments, the controller 503 may include a processor, memory, transceiver, antenna, for carrying out steps of the methods as described herein. As discussed above, a closed-loop system may be provided such that the controller 503 is operably coupled to the pump, pressure sensor, or interrogation unit.

Although the invention is described in terms of a LVAD, one will appreciate that the invention may be applied equally to other implantable blood pump systems or coupled to other portions of the heart. While blood pump 502 is generally illustrated as a centrifugal blood pump, it should be understood that blood pump may have other configurations (e.g., axial flow or mixed flow blood pumps).

Further, the invention is described in terms of comparing the estimated parameters of a patient's PA pressure curve and an ideal PA pressure curve derived from PA pressure measurements during the transient period to determine whether to adjust LVAD flow rate. However, one will appreciate that in other embodiments, comparing measured PA pressures during the stable period of a patient with stable period pressure of an ideal patient population may also be used to determine whether to adjust LVAD flow rate.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The term "or" in reference to a list of two or more items, covers all of the following interpretations of the word: any of the items in the list, all of the items in the list, and any combination of items in the list. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of controlling operation of a left ventricular assist device (LVAD) to reduce risk of right heart failure (RHF) in a patient following implantation of the LVAD, the method comprising:
controlling operation of the LVAD that is implanted in the patient to pump blood from the patient's left ventricle to the patient's aorta;
generating pulmonary artery (PA) pressure trending data for the patient via measuring pulmonary artery (PA) pressures of the patient including during the operation of the LVAD, wherein the PA pressure trending data for the patient is indicative of a variation of right ventricular afterload of the patient over a time span;
determining a regression model for the PA pressure trending data for the patient;
using the regression model to compute an estimated parameter value;
determining a deviation between the estimated parameter value and an ideal parameter value for the patient, wherein the ideal parameter for the patient is indicative of an ideal right ventricular afterload for the patient; and
controlling operation of the LVAD to adjust at least one operating parameter of the LVAD based on the deviation between the estimated parameter value and the ideal parameter value so as to reduce a deviation between the right ventricular afterload of the patient and the ideal right ventricular afterload for the patient.

2. The method of claim 1, further comprising determining a goodness of fit of the regression model of the PA pressure trending data for the patient prior to determining the deviation between the estimated parameter value and the ideal parameter value.

3. The method of claim 2, further comprising measuring additional PA pressures of the patient including during the operation of the LVAD in response to the goodness of fit being inadequate relative to an acceptable goodness of fit, and wherein the regression model is determined so as to account for the additional PA pressures of the patient.

4. The method of claim 1, wherein the PA pressures of the patient are measured only during a transient period of time following implantation of the LVAD.

5. The method of claim 4, wherein the transient period of time lasts for less than about 20 days following implantation of the LVAD prior to transitioning to a stable or steady state period.

6. The method of claim 1, wherein determining the deviation between the estimated parameter value and the ideal parameter value comprises computing a deviation between an estimated steady state PA pressure of the patient and an ideal steady state PA pressure for the patient, wherein the estimate steady state PA pressure of the patient is indicative of an estimated right ventricular afterload of the patient, and wherein the ideal stead state PA pressure for the patient is indicative of the ideal right ventricular afterload for the patient.

7. The method of claim 6, wherein the controlling operation of the LVAD to adjust at least one operating parameter of the LVAD comprises increasing a flow rate of the LVAD in response to the estimated steady state PA pressure of the patient being greater than the ideal steady state PA pressure for the patient by at least an upper threshold pressure deviation value.

8. The method of claim 6, wherein the controlling operation of the LVAD to adjust at least one operating parameter of the LVAD comprises decreasing a flow rate of the LVAD in response to the estimated steady state PA pressure of the patient being less than the ideal steady state PA pressure for the patient by at least a lower threshold pressure deviation value.

9. The method of claim 1, wherein the controlling operation of the LVAD to adjust at least one operating parameter of the LVAD comprises adjusting at least one of a flow rate of the LVAD, a pump speed of the LVAD, or a pumping operation mode of the LVAD.

10. The method of claim 9, wherein the controlling operation of the LVAD to adjust at least one operating parameter of the LVAD comprises adjusting the pumping operation mode of the LVAD.

11. The method of claim 1, wherein the regression model is defined by: $p(t)=p_\infty+e^{-\alpha t}(p_0-p_\infty)$, wherein:
p(t) are the measured PA pressures of the patient over the time span;
$p_0$ is estimated baseline PA pressure of the patient prior to implantation of the LVAD in the patient;
$p_\infty$ is estimated steady state PA pressure; and
$\alpha$ is an estimated time constant.

12. The method of claim 1, wherein the measured PA pressures of the patient are wirelessly transmitted by pressure sensor implanted within the pulmonary artery or an interrogation unit associated with the pressure sensor.

13. The method of claim 1, further comprising determining a responsiveness of the patient to the LVAD based on the determined deviation prior to the controlling operation of the LVAD to adjust the at least one operating parameter of the LVAD.

14. The method of claim 1, wherein each of the estimated parameter value and the ideal parameter value comprise a respective time parameter value.

15. The method of claim 1, wherein at least one of an external heart blood pump controller, an implantable heart blood pump controller, or an external computing device perform the method.

16. The method of claim 1, wherein the controlling of the LVAD to adjust the at least one operating parameter of the LVAD stabilizes PA pressures of the patient within a desired range for a stabilization period following a transient period.

17. The method of claim 1, further comprising outputting at least one of a visual, audio, or haptic alert prior to the controlling of the LVAD to adjust the at least one operation parameter of the LVAD.

18. The method of claim 1, wherein the PA pressure trending data for the patient comprises PA mean pressures for the patient.

* * * * *